US010184910B2

(12) United States Patent
Lammel et al.

(10) Patent No.: US 10,184,910 B2
(45) Date of Patent: Jan. 22, 2019

(54) COMBINED PRESSURE AND HUMIDITY SENSOR

(71) Applicants: Robert Bosch Tool Corporation, Broadview, IL (US); Robert Bosch GmbH, Stuttgart (DE)

(72) Inventors: Gerhard Lammel, Tuebingen (DE); Sibylle Waffenschmidt, Gomaringen (DE); Ando Feyh, Palo Alto, CA (US); Gary O'Brien, Palo Alto, CA (US); Andrew Graham, Redwood City, CA (US)

(73) Assignee: Robert Bosch GmbH, Stuttgart (DE)

( * ) Notice: Subject to any disclaimer, the term of this patent is extended or adjusted under 35 U.S.C. 154(b) by 548 days.

(21) Appl. No.: 14/062,886

(22) Filed: Oct. 25, 2013

(65) Prior Publication Data
US 2014/0116122 A1 May 1, 2014

Related U.S. Application Data

(60) Provisional application No. 61/718,416, filed on Oct. 25, 2012.

(51) Int. Cl.
*G01N 27/04* (2006.01)
*G01N 27/22* (2006.01)
(Continued)

(52) U.S. Cl.
CPC ........ *G01N 27/041* (2013.01); *G01L 19/0092* (2013.01); *G01N 27/223* (2013.01);
(Continued)

(58) Field of Classification Search
CPC . G01L 19/0092; G01L 19/141; G01N 27/041; G01D 3/0365
See application file for complete search history.

(56) References Cited

U.S. PATENT DOCUMENTS 5,074,152 A * 12/1991 Ellner ................ G01L 9/0054
73/708
5,920,392 A * 7/1999 Tsai ................... G01B 9/0207
356/498
(Continued)

FOREIGN PATENT DOCUMENTS

DE 102010043062 A1 5/2012
DE 102010062802 A1 6/2012

OTHER PUBLICATIONS

Invitation to Pay Additional Fees and Partial International Search Report corresponding to PCT Application No. PCT/US2013/066825, dated Mar. 24, 2014 (5 pages)
(Continued)

Primary Examiner — Lisa Caputo
Assistant Examiner — Herbert K Roberts
(74) Attorney, Agent, or Firm — Maginot Moore & Beck LLP

(57) ABSTRACT

A sensor device package includes a pressure sensor and a humidity sensor mounted on the same substrate and in the same housing with light protection for the pressure sensor a media opening for gas exchange for the humidity sensor. Light protection and rapid response times are provided through strategic positioning of the media opening, strategic arrangement of the pressure sensor, humidity sensor, and the media opening, and/or the use of opaque materials.

10 Claims, 3 Drawing Sheets

(51) Int. Cl.
 *G01D 3/036* (2006.01)
 *G01L 19/14* (2006.01)
 *G01L 19/00* (2006.01)
(52) U.S. Cl.
 CPC ........ *G01D 3/0365* (2013.01); *G01L 19/0038* (2013.01); *G01L 19/141* (2013.01); *G01L 19/143* (2013.01); *G01L 19/147* (2013.01); *H01L 2224/16225* (2013.01); *H01L 2224/32145* (2013.01); *H01L 2224/48091* (2013.01); *H01L 2224/73253* (2013.01); *H01L 2224/73265* (2013.01); *H01L 2924/15174* (2013.01)

(56) References Cited

U.S. PATENT DOCUMENTS

| | | | | |
|---|---|---|---|---|
| 2002/0000649 | A1* | 1/2002 | Tilmans | B81B 7/0077 257/678 |
| 2006/0277989 | A1* | 12/2006 | Lee | G01K 1/045 73/146.8 |
| 2007/0249082 | A1* | 10/2007 | Hanaoka | B81C 1/00246 438/53 |
| 2008/0173089 | A1* | 7/2008 | Wright | G01K 7/18 73/335.04 |
| 2009/0288484 | A1* | 11/2009 | Selvan | G01D 11/245 73/335.02 |
| 2010/0148950 | A1* | 6/2010 | Yamaguchi | G01L 19/0609 340/442 |
| 2010/0230766 | A1* | 9/2010 | Elian | G01L 19/141 257/414 |
| 2011/0138924 | A1* | 6/2011 | Colombo | G01L 19/0092 73/756 |

OTHER PUBLICATIONS

Won, Jonghwa et al., An Integrated Sensor for Pressure, Temperature, and Relative Humidity Based on MEMS Technology, Journal of Mechanical Science and Technology, Springer, DE, vol. 20, No. 4, pp. 505-512, Feb. 7, 2006 (8 pages).

* cited by examiner

COMBINED PRESSURE AND HUMIDITY SENSOR

CROSS-REFERENCE TO RELATED APPLICATIONS

This application claims priority to U.S. Provisional Application Ser. No. 61/718,416 entitled "EM Druck Feuchtesensor" by Lammel et al., filed Oct. 25, 2012, the disclosure of which is hereby incorporated herein by reference in its entirety.

TECHNICAL FIELD

This disclosure relates generally to semiconductor devices and particularly to microelectromechanical system (MEMS) pressure and humidity sensors.

BACKGROUND

MEMS pressure sensors are typically formed of a flexible membrane suspended over a hollow space or gap that forms a sensor volume in a substrate. The flexible membrane is deflected based on the pressure differential of the gases on each side of the membrane. Sensing elements are connected to the membrane that are configured to detect the amount of deflection which can then be correlated to a pressure value for the pressure of the gas on the side of the membrane opposite the sensor volume. Sensing elements based on piezoresistive technology and capacitive sensing technology are typically used. An evaluation circuit, such an application specific integrated circuit (ASIC) is typically provided in the same package with the pressure sensor for evaluating the output of the sensing elements.

Humidity sensors are widely used in various fields to measure the amount of water vapor present in the air of a particular environment. Humidity sensors typically include a pair of electrodes separated by a dielectric material. The dielectric layer is formed of a material, such as polymer that is configured to absorb and retain water molecules at concentrations that are proportional to the ambient humidity. The water molecules alter the dielectric constant of the polymer resulting in a change in capacitance between the two electrodes. Humidity can therefore be determined by measuring the capacitance between the two electrodes and correlating the measured capacitance to a corresponding humidity value.

Sensor housings are usually provided with various openings to media entry for the sensors. The openings allow gas exchange between the interior volume of the sensor housing and the exterior atmosphere. The gas exchange allows the interior volume of the sensor housing to be at or near the ambient pressure and humidity. However, the semiconductor components of some devices are sensitive to the electromagnetic radiation, particularly infrared radiation. For example, piezoresistors can generate a photocurrent when light is incident upon the resistor. The photocurrent produces a voltage drop across the piezoresistor which can corrupt the measurement signal output by the sensor.

Therefore, care must be taken when media enters that the direct incidence of light on the chip is minimized, for example by as small an opening in the housing as possible. This requirement is in direct contrast to other sensor devices which benefit from having larger media openings and are not susceptible to incident light. For example, humidity sensors based on the capacitive measurement principle typically have large openings in the housing positioned directly above the sensor chip for rapid response times.

The competing requirements of smaller openings and limited light exposure for sensor chips, such as pressure sensors and ASICs, and larger openings with no limit on light exposure for sensor devices, such as humidity sensors, has made it difficult to combine such devices into the same package in a manner that enables smaller package sizes to be fabricated in a cost-effective manner.

DETAILED DESCRIPTION

Figure 1:
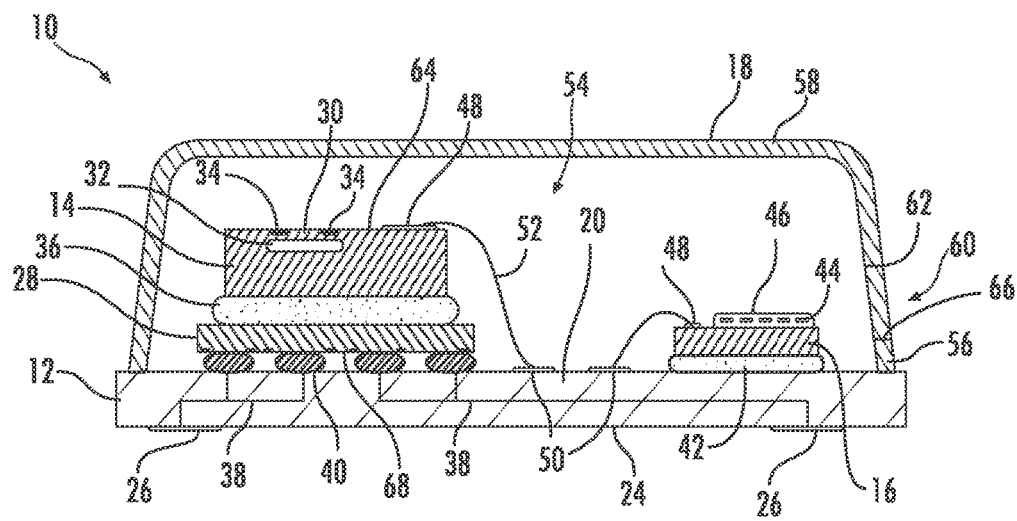
FIG. 1 depicts a cross-sectional view through a combined pressure and humidity sensor with a lateral opening in the housing cover as the media entry point.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to a person of ordinary skill in the art to which this disclosure pertains.

This disclosure is directed to combining MEMS pressure and humidity sensors on the same substrate and in the same housing with protection for the pressure sensor from incidence of light and good media entry for gas exchange for the humidity sensor. As explained below, the combined pressure and humidity sensor devices provide light protection and media entry in various ways, such as by strategic positioning of the opening, the arrangement of the sensor components in relation to the opening, and add light blocking properties to commonly used fabrication materials. By enabling MEMS pressure and humidity sensors to be combined in the same package without sacrificing functionality, smaller device sizes are possible and fewer requirements are imposed on the final product. For example, combined pressure and humidity sensors can be incorporated into consumer devices, such as mobile telephones, and require fewer openings for sensor input while taking up less space. Also, a single evaluation circuit can be used for both sensors in the device which is cost-effective as a separate evaluation circuit, or ASIC, does not have to be provided for each sensor. The combined device can also be easily protected against electromagnetic (EM) radiation by providing a grounded EM shield layer on the backside of the MEMS elements.

Referring to FIG. 1, a first embodiment of a combined pressure and humidity sensor device 10 in accordance with the disclosure is depicted. The device 10 includes a substrate 12, a pressure sensing device 14, a humidity sensing device 16, and a cover 18. The substrate 12 comprises a complementary metal-oxide-semiconductor (CMOS) substrate formed of a material, such as oxidized silicon. The substrate 12 has an upper surface 20 with electrical contacts, such as bond pads, for connecting to the sensor components. The substrate also has a bottom surface 24 with electrical contacts 26, e.g., for surface mounting, for connection to external components. In the embodiment of FIG. 1, the substrate 12 is fabricated with land grid array (LGA) technology and includes a grid of contact pads 26, or lands, on the bottom surface 24 of the substrate. In alternative embodiments, other contact types and methods may be used.

The pressure sensing device 14 comprises a MEMS pressure sensor. The pressure sensor 14 is mounted onto an evaluation circuit chip 28. The pressure sensor 14 includes a flexible membrane 30 that is suspended over a hollow space 32. The hollow space 32 allows the membrane to deflect in a manner dependent upon a pressure differential between the pressure on one side of the membrane 30 from the atmosphere in the hollow space 32 and the pressure on the other side of the membrane 30 from the atmosphere within the sensor housing. In one embodiment, piezoresistors 34 are assigned to the membrane 30 for detecting the membrane's deflection. Alternatively, the pressure sensor may be configured to measure deflection of the membrane using capacitive transduction or other transduction principles.

The evaluation circuit 28 is provided on a semiconductor chip and may comprise an integrated circuit, such as an application specific integrated circuit (ASIC). In one embodiment, the pressure sensor 14 is connected to the evaluation circuit via an adhesive layer 36. As can be seen in FIG. 1, the contacts on the upper surface 20 of the substrate are electrically connected to the contact pads 26 on the bottom surface 24 of the substrate via internal conductive pathways 38 in the substrate 12.

In the embodiment of FIG. 1, the evaluation circuit 28 is connected to the wiring contacts on the substrate 12 using flip-chip technology. The connections are formed by contact elements 40, such as solder balls, solder bumps, and the like. The contact elements 40 also function as spacer elements between the evaluation circuit 28 and the substrate 12 which help to thermally isolate the evaluation circuit from the substrate and decouple the evaluation circuit from mechanical stress on the substrate.

In FIG. 1, the humidity sensor 16 is provided on a separate chip which is mounted to the upper surface 20 of the substrate 12 alongside the pressure sensor 14/evaluation circuit 28 device. The humidity sensor 16 is attached to the upper surface 20 of the substrate using an adhesive material 42. The humidity sensor 16 includes electrodes 44, such as interdigital electrodes, that are separated by a moisture sensitive dielectric material 46. The dielectric material 46 comprises material, such as polymer, configured to absorb and retain water molecules at concentrations that are proportional to the ambient humidity. The water molecules alter the dielectric constant of the dielectric material. This enables the humidity to be determined by measuring the capacitance between the electrodes 44 and correlating the measured capacitance to a corresponding humidity value.

The evaluation circuit 28 is also configured to receive the sensor output of the humidity sensor 16. The humidity sensor 16 can be connected to the evaluation circuit via the pressure sensor and/or the substrate 12. In the embodiment of FIG. 1, the humidity sensor 16 includes a contact pad 48 that is electrically connected to an electrical connection contact pad 50 on the upper surface 20 of the substrate 12 by a bond wire 52. The pressure sensor also includes a contact pad 48 that is electrically connected to an electrical connection contact pad 50 on the upper surface 20 of the substrate 12 with a bond wire 52.

The housing cover 18 is secured to the substrate 12 extending over and around the sensor devices 14, 16. The housing cover 18 and the upper surface 20 of the substrate 12 surround and define an interior volume 54 in which the sensor components are positioned. The housing cover 18, is comprised of one or more suitable housing materials, such as plastic and/or elastomer, and may be formed using injection molding and/or extrusion coating, as examples.

The housing cover 18 includes a generally vertical sidewall portion 56 and a generally horizontal outer wall or ceiling portion 58. The vertical sidewall portion 56 extends upwardly from the upper surface 20 of the substrate 12 and defines a perimeter around the sensor components. The outer wall portion 58 extends from the sidewall portion 56 over the sensor components 14, 16 to enclose the interior volume 54 of the sensor.

The housing cover 18 includes a media opening 60 that connects the interior volume 54 of the package to the atmosphere external to the package. The media opening 60 provides a channel for gas exchange between the interior volume 54 of the sensor housing and the ambient environment. This allows the interior volume 54 of the sensor housing to exhibit ambient pressure and humidity conditions. The media opening is sized to enable gas exchange at a rate that allows pressure and humidity changes to occur within a desired time period to produce a desired sensor response.

In the embodiment of FIG. 1, the media opening 60 is provided in the sidewall portion 56 of the housing cover 18 so it is positioned laterally from the sensor components 14, 16 on the substrate. This prevents a direct incidence of light onto the light sensitive elements of the pressure sensor 14 and evaluation circuit 28. In addition, the evaluation chip 28 is mounted with the light-sensitive circuit side at the bottom facing the substrate 12 and with the pressure sensor mounted on top of the evaluation chip. This arrangement provides more light protection for the evaluation circuit than is provided by prior art arrangements in which the evaluation circuit is situated on top and connected to the substrate with bonding wires.

The pressure sensor 14 is mounted on top of the evaluation chip with the pressure (and light) sensitive side facing away from the substrate 12. To protect the upper side of the pressure sensor 14 from the direct incidence of light via the media opening 60, the media opening 60 is situated in the sidewall 56 of the cover 18 such that the upper extent 62 of the media opening 60 is positioned vertically lower than (i.e., below) the upper surface 64 of the pressure sensor. In addition, the lower extent 66 of the media opening is positioned vertically above the light sensitive lower surface 68 of the evaluation circuit 28. In other words, the upper surface 64 of the pressure sensor 14 is spaced farther apart from the upper surface 20 of the substrate 12 than the upper extent 62 of the media opening 60, and the lower extent 66 of the media opening 60 is spaced farther apart from the upper surface 20 of the substrate 12 than the lower surface 68 of the evaluation circuit 28. As a result, the direct incidence of light is prevented for both pressure sensor and the evaluation circuit.

In addition, the media opening 60 is located as close as possible to the humidity sensor 16 to allow early exposure of the moisture-sensitive material 46 of the humidity sensor 16 to atmospheric conditions entering the interior volume 54 of the sensor for faster response times. The media opening 60 is situated in the physical vicinity of the moisture-sensitive material 46 of the humidity sensor. In the embodiment of FIG. 1, the moisture sensitive material 46 is spaced a distance from the upper surface 20 of the substrate 12 that is between the distances of the upper extent 62 and the lower extent 66 of the media opening 60 from the upper surface 20 of the substrate.

The media opening 60 is also positioned farther away from the pressure sensor 14 and evaluation circuit 28 than the humidity sensor 16 to minimize the chance of stray light reaching the sensitive circuit elements of the pressure sensor 14 and evaluation circuit 28. In the embodiment of FIG. 1, the pressure sensor 14 and evaluation circuit 28 are arranged on an opposite side of the humidity sensor 16 from the media opening 60.

Figure 2:
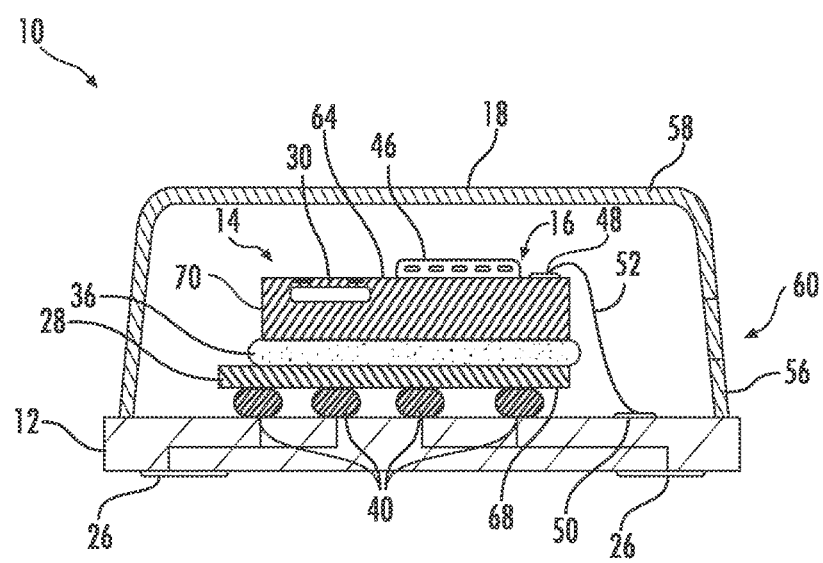
FIG. 2 depicts an alternative embodiment of the sensor of FIG. 1 with monolithically integrated sensor elements.

FIG. 2 depicts an alternative embodiment of the sensor device of FIG. 1. In the device of FIG. 2, the pressure sensor and humidity sensor are integrated, e.g., monothically, into the same chip 70. In this embodiment, the pressure sensor 14 and humidity sensor 16 are provided in the chip 70 with the pressure membrane 30 of the pressure sensor 14 laterally offset from the moisture-sensitive material 46 of the humidity sensor 16.

In FIG. 2, the sensor chip 70 is connected to an evaluation circuit chip 28 by, e.g., an adhesive layer 36. Similar to FIG. 1, the evaluation circuit 28 is connected to the wiring contacts on the substrate using flip-chip technology. The connections are formed by contact elements 40, such as solder balls, solder bumps, and the like. A contact pad 48 on the sensor chip 70 is electrically connected to the a contact pad 50 on the upper surface 20 of the substrate via a bond wire 52.

The media opening 60 is located in the sidewall portion 54 of the housing cover 18 at the same position in relation to the upper surface 64 of the chip 70 and the lower surface 68 of the evaluation circuit 28. In addition, the humidity sensor portion 16 of the sensor chip 70 is oriented toward the media opening 60 while the pressure sensor portion 14 of the sensor chip 70 is oriented away from the media opening 60.

Figure 3:
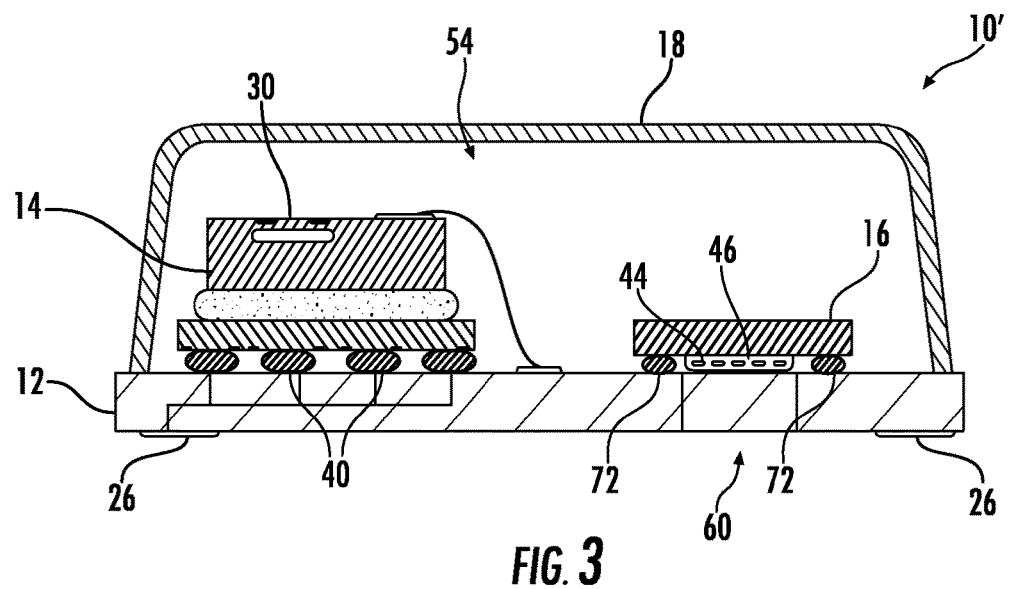
FIG. 3 depicts a cross-sectional view through a combined pressure and humidity sensor with an opening in the substrate as the media entry point.

FIG. 3 depicts another alternative embodiment of a combined pressure and humidity sensor 10' with light protection and good media entry. In the embodiment of FIG. 3, the humidity sensor 16 is mounted to the upper surface 20 of the substrate 12 with the moisture-sensitive material 44 and electrodes 44 of the humidity sensor 16 facing down toward the upper surface 20 of the substrate 12. The humidity sensor 16 may be mounted to the substrate using flip-chip technology with solder balls or bumps 72 that serve to both electrically connect the sensor 16 to the substrate 12 and to space the moisture-sensitive material 16 of the humidity sensor 16 apart from the substrate 12.

In the embodiment of FIG. 3, the media opening 60 extends through the substrate 12 directly beneath the humidity sensor 16 and the moisture-sensitive material 46. Similar to the embodiment of FIGS. 1 and 2, the media opening 60 enables gas exchange with the interior volume 54 of the sensor and is located proximate the moisture-sensitive material 46 to allow faster response times for the humidity sensor.

In another embodiment (not depicted), the evaluation circuit may be monothically integrated onto the same chip with the evaluation circuit with the evaluation circuit and humidity sensor chip mounted to the upper surface of the substrate using flip-chip technology and with the moisture-sensitive material of the humidity sensor facing the substrate as depicted in FIG. 3. In this embodiment, the lateral extent of the media opening can be limited so that it extends only under the moisture-sensitive material and not under the evaluation circuitry.

Figure 4:
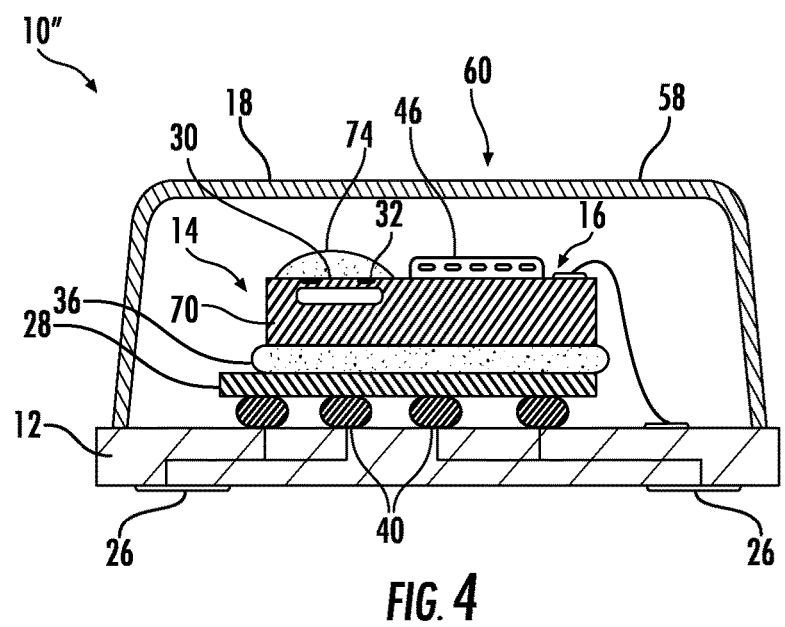
FIG. 4 depicts a cross-sectional view through a combined pressure and humidity sensor with a top opening in the housing cover as the media entry point and opaque gel as the light protection means on the pressure sensor element.

FIG. 4 depicts another embodiment of a combined pressure and humidity sensor 10" with light protection and good media entry. In this embodiment, the pressure and humidity sensor 14, 16 are depicted as being monothically integrated onto the same chip 70 with the pressure membrane 30 of the pressure sensor 14 and the moisture-sensitive material 46 of the humidity sensor 16 laterally offset from each other on the top side of the chip 70. Similar to FIG. 2, the sensor chip 70 of the device of FIG. 4 is mounted onto the evaluation circuit, e.g., using an adhesive layer 36, and the evaluation circuit 28 is mounted to the substrate 12 using flip-chip technology.

In FIG. 4, the media opening 60 is provided through the outer wall or ceiling 58 of the housing cover 18 directly over the moisture-sensitive material 46 of the humidity sensor 16. The media opening 60 does not extend laterally over the pressure sensor portion 14 of the chip. To further protect the light-sensitive elements of the pressure sensor 14 from incident light, a flexible material 74 that is opaque to infrared radiation is added to the pressure sensor 14 over the membrane 30 and/or over the piezoresistors 32.

In one embodiment, the opaque material 74 comprises a gel, such as silicone gel, mixed with dark, e.g., black, dye. Gel without an opaque dye is commonly used in pressure sensors and other semiconductor devices as a protective material (e.g., corrosion and damping) that will not significantly hamper the sensor response. By mixing the gel with an opaque dye, the gel 74 will have light blocking properties that can protect the pressure sensor 14 from incident light via the media opening.

In another embodiment, opaque properties may be provided by configuring certain layers of the pressure sensor 14 to serve as light protection during the fabrication process of the pressure sensor. For example, highly doped polysilicon or thin metal layers may be formed over the p/n junctions of the piezoresistors 32 to serve as light protection. Although the sensor chip in FIG. 4 has been described as being monothically integrated chip, the position of the media opening 60 and use of opaque materials for the pressure sensor can be adapted for use in embodiments in which the pressure sensor and humidity sensor are provided in separate chips as depicted in FIG. 1.

Figure 5:
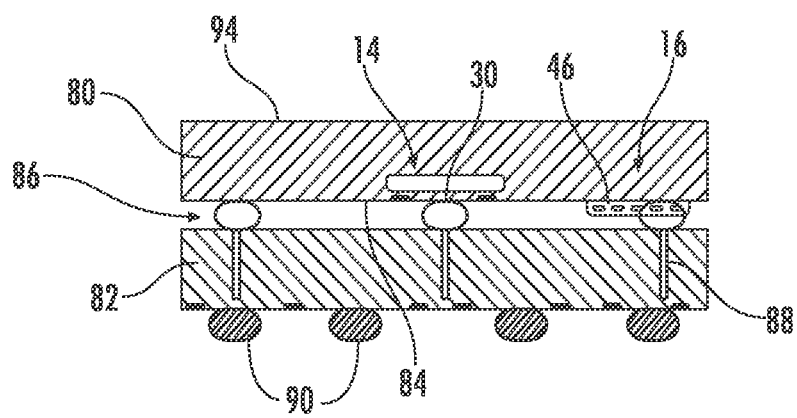
FIG. 5 depicts a cross-sectional view through a combined pressure and humidity sensor in a chip scale package with a lateral media entry point.
Figure 6:
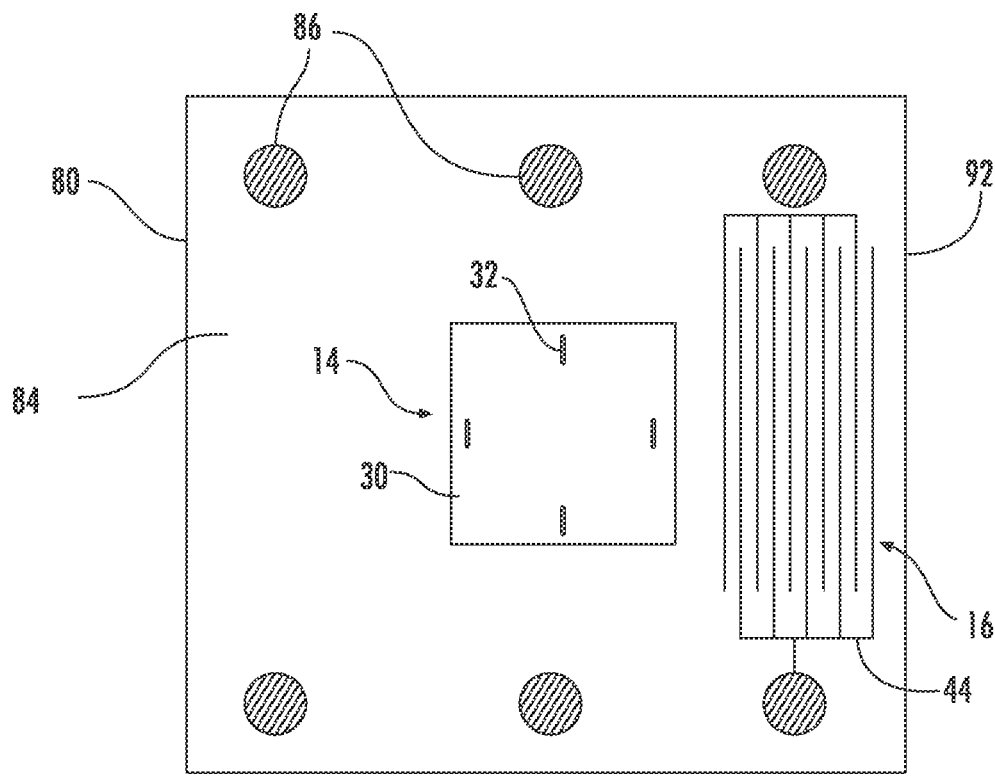
FIG. 6 depicts a plan view of the combined pressure and humidity sensor of FIG. 5.

Another embodiment of a combined pressure and humidity sensor with light protection and good media entry is depicted in FIGS. 5 and 6. In the embodiment of FIGS. 5 and 6, an integrated pressure sensor and humidity sensor chip 80 is connected to an evaluation circuit chip 82 without a further substrate. This configuration enables a chip scale package to be formed. Chip scale packaging is a type of integrated circuit package with industry imposed requirements, such as the package must have an area no greater than 1.2 times that of the die and it must be a single-die, direct surface mountable package.

Referring to FIG. 5, the functional side 84 of the pressure and humidity sensor chip 80 is arranged facing the evaluation circuit chip 82, or ASIC. In this embodiment, the ASIC 82 serves as a rigid interposer and includes connection elements 86, such as balls or pads, on the upper surface of the ASIC for connection to the sensor chip 80. The ASIC 82 also includes through silicon vias 88 which electrically connect the connection elements 86 on the front side of the ASIC to connection contacts 90 on the back side of the ASIC In the embodiment of FIGS. 5 and 6, the connection elements 86 space the functional side 84 of the sensor chip 80 apart from the ASIC 82 to allow media to pass laterally between the sensor chip 80 and ASIC 82. As can be seen in FIG. 6, the humidity sensor 16 is arranged on the functional side 84 between one edge 92 of the chip 80 and the pressure sensor 14 in the center of the chip 80. This positioning allows rapid media exposure of the moisture-sensitive material of the humidity sensor for faster sensor response times.

To maximize light protection for the pressure sensor in this arrangement, the pressure sensor 14 is situated in the center of the functional side 84 of the sensor chip 80 as depicted in FIG. 6. By positioning the pressure sensor 14 in the center, the pressure sensor 14 is protected equally from light coming from each side of the package.

In the embodiment of FIGS. 5 and 6, the backside 94 (FIG. 5) of the MEMS element can be configured to serve as an electromagnetic (EM) shield for the device. For example, in one embodiment, a highly doped layer of material, such as polysilicon, can be provided on the backside of the MEMS and connected to ground. This forms a Faraday cage which can shield the sensor chip/ASIC from external EM radiation. As alternatives to a highly doped polysilicon layer, metallic films or a silicide layer may be added to the backside of a MEMS chip and grounded to provide EM protection.

Such EM protection is beneficial in chip scale packaging and can also be beneficial in the other packaging embodiments described above. Depending on the chosen packaging configuration, the backside of the ASIC can also be configured as a Faraday cage, e.g., using a grounded highly doped layer, metallic films, a silicide layer. In some cases, it may also be possible to use a part of the MEMS front side as a Faraday cage being highly conductive and grounded by above-mentioned methods.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A semiconductor package comprising:
   a substrate having an upper surface and a lower surface;
   a housing cover having a sidewall portion attached to the substrate and a ceiling portion extending over the upper surface of the substrate, the substrate and the housing cover forming a housing that surrounds and defines a single shared, undivided interior volume;
   a pressure sensor device mounted onto the substrate within the interior volume, the pressure sensor having a top side including a flexible membrane suspended over a hollow space;
   a humidity sensor device mounted onto the substrate within the interior volume with the pressure sensor and including a moisture-sensitive material;
   an evaluation circuit device mounted onto the substrate within the interior volume with the pressure sensor and the humidity sensor and electrically connected to the pressure sensor and the humidity sensor;
   a media opening in the housing that enables gas exchange between the interior volume and an exterior of the housing,
   wherein the housing cover is spaced apart from each of the pressure sensor, the humidity sensor and the evaluation circuit such that an open space is formed within the interior volume between the housing cover and each of the pressure sensor, the humidity sensor and the evaluation circuit, the media opening being in communication with the open space such that atmospheric conditions within the open space correspond to atmospheric conditions outside of the housing cover,
   wherein the flexible membrane is arranged facing the ceiling portion of the housing cover with the hollow space positioned on an opposite side of the flexible membrane from the ceiling portion such that the flexible membrane is exposed directly to the open space of the interior volume,
   wherein the media opening is positioned closer to the moisture-sensitive material of the humidity sensor than the flexible membrane of the pressure sensor, and
   wherein the media opening is positioned in the housing at a location that is offset laterally from the pressure sensor device and closer to the upper surface than the top side of the pressure sensor device.

2. The package of claim 1, wherein the media opening extends through the sidewall portion of the housing cover,
   wherein the top side of the pressure sensor is spaced farther apart from the substrate than an upper extent of the media opening in the sidewall.

3. The package of claim 2, wherein a lower extent of the media opening in the sidewall is spaced farther apart from the substrate than a lower surface of the evaluation circuit.

4. The package of claim 3, wherein the pressure sensor is provided on a first chip and the evaluation circuit is provided on a second chip, and
   wherein the first chip is mounted onto the second chip.

5. The package of claim 4, wherein the second chip is electrically connected to the substrate using flip-chip technology.

6. The package of claim 5, wherein the humidity sensor is provided on a third chip, the third chip being mounted to the substrate alongside the first and the second chips, and
   wherein the third chip is positioned proximate the media opening and the first and second chips are positioned farther away from the media opening than the third chip.

7. The package of claim 5, wherein the humidity sensor is integrated onto the first chip with the pressure sensor, the humidity sensor being laterally offset from the pressure sensor in the first chip, and
   wherein the first chip is positioned with the humidity sensor oriented toward the media opening and the pressure sensor oriented away from the media opening.

8. The package of claim 1, wherein the media opening extends through the substrate directly beneath the humidity sensor device.

9. The package of claim 8, wherein the pressure sensor is provided on a first chip and the evaluation circuit is provided on a second chip, the first chip being mounted on top of the second chip, the second chip being mounted to the substrate,
   wherein the humidity sensor is provided on a third chip, the third chip being mounted to the substrate alongside the first and the second chips, and
   wherein the humidity sensor is oriented with the moisture-sensitive material facing toward the substrate and positioned above the media opening.

10. The package of claim 9, wherein the third chip is mounted to the substrate using flip-chip technology.

\* \* \* \* \*